United States Patent [19]

Peratello et al.

[11] Patent Number: 5,342,814
[45] Date of Patent: Aug. 30, 1994

[54] EXTRUDED CATALYST BASED ON SILICA/ALUMINA GEL, AND PROCESS FOR PREPARING IT

[75] Inventors: Stefano Peratello, Nova Milanese; Carlo Perego, Carnate; Giuseppe Bellussi, Piacenza, all of Italy

[73] Assignees: Eniricerche S.p.A.; Euron S.p.A.; Snamprogetti, S.p.A., all of Milan, Italy

[21] Appl. No.: 985,552

[22] Filed: Dec. 3, 1992

[30] Foreign Application Priority Data

Dec. 6, 1991 [IT] Italy ............................ MI91A003276

[51] Int. Cl.$^5$ ........................ B01J 21/12; B01J 37/00
[52] U.S. Cl. ..................................... 502/263; 502/238
[58] Field of Search ................................ 502/263, 238

[56] References Cited

U.S. PATENT DOCUMENTS

| | | | |
|---|---|---|---|
| 4,174,301 | 11/1979 | Choca et al. | 252/455 R |
| 4,238,361 | 12/1980 | Alafandi et al. | 252/438 |
| 4,277,376 | 7/1981 | Paolasini | 502/263 |
| 4,708,945 | 11/1987 | Murrell et al. | 502/263 |
| 5,049,536 | 9/1991 | Bellussi et al. | 502/263 |
| 5,051,386 | 9/1991 | Ward et al. | 502/64 |

FOREIGN PATENT DOCUMENTS

| | | |
|---|---|---|
| 0160145 | 11/1985 | European Pat. Off. . |
| 0340868 | 11/1989 | European Pat. Off. . |
| 0014599 | 6/1979 | Japan ................................. 502/263 |
| 0187337 | 9/1985 | Japan ................................. 502/263 |
| 1413874 | 11/1975 | United Kingdom ................ 502/263 |

OTHER PUBLICATIONS

Mark R. S. Manton et al., Journal of Catalysis: Controlled Pore Sizes and Active Site Spacings Determining Selectivity in Amorphous Silica–Alumina Catalysts, vol. 60, pp. 156–166 (1979).

*Primary Examiner*—Carl F. Dees
*Attorney, Agent, or Firm*—George P. Hoare, Jr.

[57] ABSTRACT

The preparation is disclosed of an extruded catalyst based on a silica/alumina gel, which catalyst is particularly active in acid-catalyzed reactions, such as the oligomerization of light olefins, e.g., propylene.

17 Claims, No Drawings

EXTRUDED CATALYST BASED ON SILICA/ALUMINA GEL, AND PROCESS FOR PREPARING IT

The present invention relates to a catalyst in extruded form, based on silica/alumina gel, and to the process for preparing it. The invention also relates to the use of such a catalyst in olefin oligomerization processes.

Some silica/alumina gels, of amorphous character, displaying catalytic activity, are known in the art. So, e.g., European patent application published with publication No. 160,145 discloses a process of alkylation of aromatic hydrocarbons which uses a catalyst consisting of a silica/alumina gel, of amorphous character, with pore diameter typically comprised within the range from of 50 to 500 Angstrom, and with a ratio of silica to alumina typically comprised within the range of from 1:1 to 10:1. M. R. S. Manton and J. Davidtz in Journal of Catalysis, 60, 156–166 (1979) describe a process for the synthesis for amorphous silica/alumina catalysts, having a controlled pore diameter. Typically, these catalysts display pores with diameter comprised within the range of from 3.7 to 15 nm.

European patent application No. 340,868 discloses a silica/alumina gel, amorphous X rays, having a molar ratio of $SiO_2/Al_2O_3$ of from 30:1 to 500:1, with a specific surface area comprised within the range of from 500 to 1000 m$^2$/g, a total pore volume of from 0.3 to 0.6 ml/g, and substantially free from pores with larger diameters than 30 Angstrom.

However, the problem exists of rendering industrially useable the silica/alumina gel disclosed in the above said patent application by endowing it with adequate properties of mechanical strength, without endangering the high catalytic performance thereof.

Those skilled in the art are aware of the possible procedures for preparing extruded bodies having high enough mechanical strength values, with their catalytic performance being the same. Thus, for example, the catalyst can be ground, so as to obtain powders consisting of particles with an average size comprised within the range of from 5 to 50 microns, and subsequently blending them with a thickener, for example, stearine, glycerol, methylcellulose.

According to another route of preparation of the extruded catalyst, the catalyst is ground and then is suspended, with vigourous stirring, in an aqueous solution of a soluble aluminum salt. The addition of a base makes it possible for aluminum hydroxide to be precipitated, with the catalyst particles becoming embedded inside said precipitate particles. A further method consists in mixing silica/alumina gel powders with a second powder selected from metal oxides in the presence of a thickener, for example, stearine, glycerol, methylcellulose.

All of the techniques cited hereinabove should make it possible for extrudates to be obtained, which are endowed with such a high mechanical strength can be used at an industrial level, with the catalytic properties of silica/alumina gel remaining unchanged.

It has been found now that one of the above said techniques leads to catalysts showing the necessary mechanical strength, but which, surprisingly, are more active in catalyzing the usual petrochemical acid-catalyzed reactions, such as alkylation, isomerization and oligomerization.

In accordance therewith, according to a first aspect thereof, the present invention relates to a catalyst consisting of:
an inert binding agent, and
a catalytically active portion, constituted by a silica/alumina gel, amorphous at X rays, with $SiO_2/Al_2O_3$ being a molar ratio comprised within the range of from 30:1 to 500:1, having a total pore volume comprised within the range of from 0.3 to 0.6 ml/g, and substantially free from pores having a greater average diameter than 30 Angstrom, characterized in that:
the inert binding agent is constituted by alumina grades belonging to the class of bohemite or of pseudobohemite.

The aluminas used in the present invention as binding agents in order to extrude the silica/alumina gel have the general formula

AlO—OH.

In the preferred embodiment of the present invention, bohemite or pseudobohemite have an average diameter of less than 50 microns, and are present in a ratio to silica/alumina gel comprised within the range of from 0.2 to 2.5% by weight.

The catalyst according to the present invention is suitably prepared by means of a first mechanical mixing of the active phase, (i.e., of silica/alumina gel ground to a powder having an average diameter of less than 50 microns), with the inert binding agent belonging to the class of bohemites or pseudobohemites, or mixtures thereof.

The mixing of the active phase with the inert binding agent is carried out in the presence of a large enough amount of thickener so as to produce a paste having the desired viscosity. The mixing is continued until a homogeneous phase is formed. The thickener may be water, an aqueous solution of methylcellulose, stearine, glycerol and so forth. The thickener contains a mineral or organic acid in an amount comprised within the range of from 0.5 to 8 grams of acid per 100 g of inert binding agent. According to alternate practical embodiment, the acid is added to the paste and the resulting mixture is homogenized.

The resulting paste is then extruded and cylindrical bodies of catalyst are obtained, the dimensions of which may be varied as a function of the application requirements.

The extrudate is subsequently submitted to ageing at a temperature of from 10° to 40° C. and then to drying at 100°–120°C.

The final step consists of the calcination in air at a temperature comprised within the range of from 500° to 600° C.

The catalyst obtained in that way displays a higher catalytic activity than the catalytic activity of the silica/alumina gel used as the starting materials, and the catalyst furthermore is useable at an industrial level because it has an axial breaking strength comprised within the range of from 20 to 80 kg/cm$^2$ and a radial breaking strength comprised within the range of from 3 to 8.5 kg/cm.

Important features of the catalyst according to the present invention are the bimodal distribution of porosity, a surface area comprised within the range of from 300 to 600 m$^2$/g, and a high acidity.

The catalyst according to the present invention can be suitably used in the usual petrochemical acid-catalyzed reactions, such as alkylation, isomerization and oligomerization of light olefins, in particular of propylene.

In particular, the catalyst according to the present invention is very effective in the oligomerization of light olefins, in particular propylene, in order to yield hydrocarbon cuts showing extremely good qualities as gasoline and jet fuel.

The following experimental examples are reported in order to illustrate the present invention in greater detail.

EXAMPLE 1

Catalyst preparation 40 g of Al—Si gel, prepared as disclosed in European patent application No. 340,868, is ground in a ball mill 1 and t hen is micronized until a powder is obtained with an average distribution of particles comprised within the range of from 10 to 50 microns. To such a powder, 40 g of a commercial pseudobohemite (CATAPAL B-VISTA CHEMICAL COMPANY) is blended by means of a mechanical mixing procedure. Separately, an aqueous solution of methylcellulose (METOCEL FLUKA 64625) at 1% by weight is prepared and is acidified with 0.63 g of glacial $CH_3COOH$ (99.8% by weight).

The acidified aqueous methylcellulose solution (60-70 g) and the powder are now thoroughly mixed, until a homogeneous paste is obtained.

After performing the extrusion, the extrudate is submitted to a 4-hour ageing at room temperature, the aged extrudate is dried at 100° C. for 5 hours, and the dried extrudate is calcined at 550° C. for 8 hours in air.

At the end of this operation, the catalyst shows a mechanical strength of 6.4 kg/cm in the radial direction and of 42 kg/cm$^2$ in the axial direction, and a specific surface area of 460 m$^2$/g.

EXAMPLE 2A

Propylene oligomerization

The extruded catalyst obtained as disclosed in Example 1 was tested in propylene oligomerization under the following operating conditions:
catalyst shape: cylindrical extruded body;
catalyst dimensions: average diameter approximately 3 mm, average length approximately 5 mm;
reactor type: fixed bed;
reactor dimensions: inner diameter=36 mm, length=600 mm;
feed: propylene/propane mixture in the ratio of 35:65 by weight;
reactor temperature: from 100° to 250° C.;
reactor pressure: from 30 to 50 bars;
space velocity WHSV: from 0.5 to 2 g of propylene per gram of active phase per hour.

The results are reported in Table 1.

TABLE 1

| WHSV h$^{-1}$ | Pressure bar | Temperature °C. | Conversion rate, % |
|---|---|---|---|
| 2 | 30 | 140 | 20 |
| 1 | 30 | 140 | 30 |
| 1 | 40 | 140 | 37 |
| 1 | 50 | 150 | 52 |
| 1 | 40 | 150 | 46 |
| 0.5 | 40 | 150 | 65 |

TABLE 1-continued

| WHSV h$^{-1}$ | Pressure bar | Temperature °C. | Conversion rate, % |
|---|---|---|---|
| 0.5 | 40 | 160 | 72 |

The product obtained from the oligomerization was then distilled, with a fraction useable as gasoline and a fraction useable as jet fuel being obtained.

The gasoline fraction displayed the following characteristics:

| | |
|---|---|
| RON | 96.8 |
| MON | 82.2 |
| d$_{15}$ | 0.7478 |
| C$_1$-C$_4$(% by weight) | 1 |
| 13–80° C. (% by weight) | 3.96 |
| 80–175° C. (% by weight) | 42.32 |
| 175+ (% by weight) | 45.72 |
| Olefins (% by weight) | 99 |
| Saturated compounds (% by weight) | 1 |
| Aromatics (% by weight) | 0 |

The jet fuel fraction displays the following characteristics:

| | |
|---|---|
| Aromatics, % by volume (ASTM D1319) | 1.8 |
| Freezing point, °C. (ASTM D2386) | 60 |
| Smoke point, mm (ASTM D1322) | 38 |
| Gums, mg/100 ml (ASTM D381) | 49 |
| Flash point, °C. (ASTM D3828) | 38 |
| Density at 15° C. (ASTM D1298) | 0.7718 |
| Distillation (ASTM D86): | |
| incipient boiling point (°C.) | 140 |
| 10% by volume (°C.) | 149 |
| 20% by volume (°C.) | 157 |
| 50% by volume (°C.) | 184 |
| 90% by volume (°C.) | 264 |
| end point (20 C.): | 304 |

EXAMPLE 2B

Propylene oligomerization

The extruded catalyst obtained as disclosed in Example 1 was tested in propylene oligomerization under the following operating conditions:
catalyst shape: cylindrical extruded body;
catalyst dimensions: average diameter approximately 3 mm, average length approximately 5 mm;
reactor type: fixed bed;
reactor dimensions: inner diameter=36 mm, length=600 mm;
feed: propylene/propane mixture in the ratio of 70:30 by weight;
reactor temperature: from 100° to 250° C.;
reactor pressure: 50 bars;
space velocity WHSV: 2 g of propylene per gram of active phase per hour.

The oligomerization rate was 900 g of oligomerized product per each gram of the active catalyst portion.

COMPARATIVE EXAMPLE 1

Preparation of a catalytic extrudate by mixing the active phase with a thickener 80 g of Al—Si gel, prepared as disclosed in European patent application No. 340,868, is ground in a ball mill and then is micronized until a powder is obtained which has an average particle distribution comprised within the range of from 10 to 50 microns. Such a powder is slowly added to 40 g of a water-alcohol solution of methylcellulose (METOCEL FLUKA 64625) at 1% by weight with an effective mechanical stirring. The resulting homogeneous paste is allowed to age for approximately 1 hour, then is extruded. The extrudate, having a size comprised within the range of from 3 to 5 mm, first dried at 150° C. for 5 hours and then is calcined at 500° C. for 8-10 hours. At the end of this operation, the catalyst displays a low mechanical strength.

COMPARATIVE EXAMPLE 2

Preparation of a catalytic extrudate by precipitation of aluminum hydroxide 40 g of Al—Si gel, prepared as disclosed in European patent application No. 340,868, is ground in a ball mill and then is micronized until a powder is obtained which has an average particle distribution comprised within the range of from 10 to 50 microns. The powder is added to 905.6 g of an aqueous solution of 11.6% by weight of $Al_2(SO_4)_3$, kept vigorously stirred, $NH_4OH$ at 30% by weight is added, until a pH value of 9 is obtained. The resulting precipitate is washed and filtered repeatedly, until neutral. The resulting solid material, after being dried at 100° C. for 2 hours and calcined overnight at 500° C., is ground and micronized again until granular distribution comprised within the range of from 10 to 50 microns is obtained. Such a powder is slowly added to 72 g of a water-alcohol solution of methylcellulose (METOCEL FLUKA 64625) at 1% by weight, with an effective mechanical stirring. The resulting homogeneous paste is allowed to age for approximately 1 hour, then is extruded. The extrudate, having a size comprised within the range of from 3 to 5 mm, is first dried at 150° C. for 5 hours and then is calcined at 500° C. for 8-10 hours. At the end of this operation, the catalyst displays a mechanical strength of 1.4 kg/cm in the radial direction and of 14 kg/cm$^2$ in radial direction, and a specific surface area of 333 m$^2$/g.

The resulting extrudate is tested as disclosed in Example 1 (Table 2).

TABLE 2

| WHSV h$^{-1}$ | Pressure bar | Temperature °C. | Conversion rate, % |
|---|---|---|---|
| 2 | 30 | 140 | 3 |
| 1 | 30 | 140 | 4 |
| 1 | 40 | 140 | 5 |
| 1 | 50 | 150 | 8 |
| 0.5 | 40 | 150 | 15 |
| 0.5 | 40 | 160 | 22 |

The catalyst is also tested as disclosed in Example 2B, resulting in a productivity rate of 300 g of oligomers per each gram of the catalytically active portion.

COMPARATIVE EXAMPLE 3

Preparation of unbound silica/alumina gel

The catalyst, prepared as disclosed in European patent application No. 340,868, was tested for propylene oligomerization as disclosed in Example 2A. The results are reported in Table 3.

TABLE 3

| WHSV h$^{-1}$ | Pressure bar | Temperature °C. | Conversion rate, % |
|---|---|---|---|
| 2 | 30 | 140 | 3 |
| 1 | 30 | 140 | 5 |
| 1 | 40 | 140 | 6 |
| 1 | 50 | 150 | 10 |

TABLE 3-continued

| WHSV h$^{-1}$ | Pressure bar | Temperature °C. | Conversion rate, % |
|---|---|---|---|
| 0.5 | 40 | 150 | 20 |
| 0.5 | 40 | 160 | 29 |

The data for catalytic activity sets forth the better performance of the catalyst according to the present invention as compared to the same catalyst without binding agent, as well as the catalyst obtained by means of other techniques.

We claim:
1. A catalyst consisting essentially of:
an inert binding agent, and,
as a catalytically active portion,
an amorphous silica/alumina gel, with the silica to alumina being in a molar ratio from 30:1 to 500:1, having a total pore volume of from 0.3 to 0.6 ml/g, and being substantially free from pores having an average diameter of greater than 30 Angstrom, wherein the inert binding agent is an alumina selected from the group consisting of bohemite pseudobohemite, and mixture thereof.
2. A catalyst according to claim 1, wherein the bohemite or the pseudobohemite have an average diameter of less than 50 microns and are present in a ratio to the silica/alumina gel of from 0.2 to 2.5 by weight.
3. A process for preparing the catalyst according to claim 1, comprising the steps of mixing the active portion with the inert binding agent in the presence of a thickener containing a mineral or organic acid in an amount of from 0.5 to 8 g of acid per 100 g of inert binding agent until a homogeneous paste is obtained; extruding the paste as cylindrical bodies of catalyst; ageing the cylindrical catalyst bodies at a temperature of from 10° to 40° C.; drying the aged cylindrical catalyst bodies at a temperature of from 100° to 120° C.; and calcining the dried, aged cylindrical catalyst bodies in air at a temperature of from 500° to 600° C.
4. A process for preparing the catalyst according to claim 1, comprising the steps of mixing the active portion within the inert binding agent in the presence of a thickener until a homogeneous paste is obtained; adding to the paste a mineral or organic acid in an amount of from 0.5 to 8 g of acid per 100 g of inert binding agent; then extruding the paste as cylindrical bodies of catalyst; ageing the cylindrical catalyst bodies at a temperature of from 10° to 40° C.; drying the aged cylindrical catalyst bodies at a temperature of from 100° to 120° C.; and calcining the dried, aged cylindrical catalyst bodies in air at a temperature of from 500° to 600° C.
5. A process for preparing the catalyst according to claim 2, comprising the steps of mixing the active portion with the inert binding agent in the presence of a thickener containing a mineral or organic acid in an amount of from 0.5 to 8 g of acid per 100 g of inert binding agent until a homogeneous paste is obtained; extruding the paste as cylindrical bodies of catalyst; ageing the cylindrical catalyst bodies at a temperature of from 10° to 40° C.; drying the aged cylindrical catalyst bodies at a temperature of from 100° to 120° and calcining the dried, aged cylindrical catalyst bodies in air at a temperature of from 500° to 600° C.
6. A process for preparing the catalyst according to claim 2, comprising the steps of mixing the active portion within the inert binding agent in the presence of a thickener until a homogeneous paste is obtained; adding to the paste a mineral or organic acid in an amount of from 0.5 to 8 g of acid per 100 g of inert binding agent; then extruding the paste as cylindrical bodies of catalyst; ageing the cylindrical catalyst bodies at a temperature of from 10° to 40° C.; drying the aged cylindrical catalyst bodies at a temperature of from 100° to 120° C.; and calcining the dried, aged cylindrical catalyst bodies in air at a temperature of from 500° to 600° C.

7. A catalyst according to claim 3, wherein the thickener is selected from the group consisting of water, an aqueous solution of methylcellulose, stearine, and glycerol.

8. A catalyst according to claim 4, wherein the thickener is selected from the group consisting of water, an aqueous solution of methylcellulose, stearine, and glycerol.

9. A catalyst according to claim 5, wherein the thickener is the aqueous solution of methylcellulose.

10. A catalyst according to claim 4, wherein the thickener is the aqueous solution of methylcellulose.

11. A catalyst according to claim 3, wherein the thickener is present in an amount sufficient to produce the paste having a viscosity suitable for extrusion.

12. A catalyst according to claim 4, wherein the thickener is present in an amount sufficient to produce the paste having a viscosity suitable for extrusion.

13. A catalyst according to claim 1, wherein the catalyst has an axial breaking strength of from 20 to 80 kg/cm$^2$ and a radial breaking strength of from 3 to 8.5 kg/cm.

14. A catalyst according to claim 2, wherein the catalyst has an axial breaking strength of from 20 to 80 kg/cm$^2$ and a radial breaking strength of from 3 to 8.5 kg/cm.

15. A catalyst according to claim 13, wherein the catalyst has a surface area of from 300 to 600 m$^2$/g.

16. A catalyst according to claim 14, wherein the catalyst has a surface area of from 300 to 600 m$^2$/g.

17. A catalyst according to claim 1, wherein the alumina is pseudobohemite and wherein the catalyst has an axial breaking strength of 42 kg./cm$^2$, a radial breaking strength of 6.4. kg/cm, and a surface area of 460 m$^2$/g.

* * * * *

UNITED STATES PATENT AND TRADEMARK OFFICE
CERTIFICATE OF CORRECTION

PATENT NO. : 5,342,814
DATED : August 30, 1994
INVENTOR(S) : Stefano Peratello, Carlo Perego, Giuseppe Bellussi It is certified that error appears in the above-indentified patent and that said Letters Patent is hereby corrected as shown below:

In column 2, line 26 delete "%".

Signed and Sealed this

Twenty-ninth Day of August, 1995

Attest:

BRUCE LEHMAN

*Attesting Officer*   *Commissioner of Patents and Trademarks*